United States Patent
Sato et al.

(10) Patent No.: US 10,028,564 B2
(45) Date of Patent: *Jul. 24, 2018

(54) LIQUID COSMETIC

(71) Applicant: MITSUBISHI PENCIL COMPANY, LIMITED, Shinagawa-ku (JP)

(72) Inventors: Hiroshi Sato, Fujioka (JP); Yuya Nagasaka, Fujioka (JP)

(73) Assignee: MITSUBISHI PENCIL COMPANY, LIMITED, Shinagawa-Ku, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/380,550

(22) PCT Filed: Feb. 26, 2013

(86) PCT No.: PCT/JP2013/054959
§ 371 (c)(1),
(2) Date: Aug. 22, 2014

(87) PCT Pub. No.: WO2013/129395
PCT Pub. Date: Sep. 6, 2013

(65) Prior Publication Data
US 2015/0016857 A1    Jan. 15, 2015

(30) Foreign Application Priority Data

Mar. 1, 2012    (JP) ................. 2012-045296

(51) Int. Cl.
*A45D 34/04* (2006.01)
*A61Q 1/10* (2006.01)
(Continued)

(52) U.S. Cl.
CPC ............. *A45D 34/042* (2013.01); *A61K 8/18* (2013.01); *A61K 8/19* (2013.01); *A61K 8/73* (2013.01);
(Continued)

(58) Field of Classification Search
CPC ...... A61K 8/19; A61K 8/18; A61K 2800/872; A61K 8/73; A61K 8/8158; A61K 2800/33;
(Continued)

(56) References Cited

U.S. PATENT DOCUMENTS 6,534,047 B1 *   3/2003   Bodelin ................ A61K 8/731
                                                                    424/401
7,553,100 B2 *   6/2009   Muhr-Sweeney ........ B08B 1/00
                                                                    401/17
(Continued)

FOREIGN PATENT DOCUMENTS

JP    2006-306854 A    11/2006
JP    2009-209056 A     9/2009
(Continued)

OTHER PUBLICATIONS

International Preliminary Report on Patentability (Chapter I) with Written Opinion of the International Search Authority dated Sep. 22, 2014, in International Application No. PCT/JP2013/054959 (10 pages).

(Continued)

*Primary Examiner* — David Walczak
(74) *Attorney, Agent, or Firm* — Buchanan, Ingersoll & Rooney PC

(57) ABSTRACT

Provided is a liquid cosmetic suited for a liquid cosmetic applicator using a brush or a pen feed as an applying means and suited for use in an eyeliner or an eyebrow, which has a good water resistance and is excellent in a skin adhesive property and which is free of a lustrous feeling and has a mat tone. The liquid cosmetic comprises at least carbon black, water, 0.5 to 5% by mass of a dispersant comprising a film-formable resin, 2 to 15% by mass as a solid of a film-forming agent, 0.5% by mass or less of a surfactant, and xanthan gum or a hydroxyethyl acrylate/acryloyldimethyl- (Continued)

taurinato Na copolymer for a mat tone provider; a glossiness of the liquid cosmetic is 6.5 or less; and a viscosity thereof at 25° C. and a shear rate of 76.8 s$^{-1}$ falls in a range of 10 to 270 mPa·s.

5 Claims, 2 Drawing Sheets

(51) Int. Cl.

| | | |
|---|---|---|
| A61K 8/73 | (2006.01) | |
| A61K 8/19 | (2006.01) | |
| A61K 8/81 | (2006.01) | |
| A61K 8/18 | (2006.01) | |
| A61Q 1/00 | (2006.01) | |
| A45D 34/00 | (2006.01) | |

(52) U.S. Cl.
CPC .............. *A61K 8/8158* (2013.01); *A61Q 1/00* (2013.01); *A61Q 1/10* (2013.01); *A45D 2034/007* (2013.01); *A61K 2800/33* (2013.01); *A61K 2800/87* (2013.01)

(58) Field of Classification Search
CPC .. A61K 2800/87; A45D 34/042; A45D 34/04; A45D 2034/007; A61Q 1/10; A61Q 1/00
USPC .................................................. 401/277, 424
See application file for complete search history.

(56) References Cited

U.S. PATENT DOCUMENTS

| | | | | |
|---|---|---|---|---|
| 9,016,288 B2* | 4/2015 | Wyatt | ...................... | A46B 1/00 132/218 |
| 9,113,694 B2* | 8/2015 | Azar | ...................... | A45D 40/24 |
| 2002/0006414 A1* | 1/2002 | Murata | ................ | A61K 8/0212 424/400 |
| 2002/0051756 A1* | 5/2002 | Sato | .................... | A45D 34/042 424/61 |
| 2004/0229976 A1* | 11/2004 | Kakiuchi | ............. | C09D 11/322 523/160 |
| 2006/0088484 A1* | 4/2006 | Thevenet | ............... | A45D 33/00 424/61 |
| 2007/0009454 A1* | 1/2007 | Thevenet | ................. | A61K 8/19 424/61 |
| 2007/0212316 A1* | 9/2007 | Feng | .................... | A61K 8/8152 424/70.7 |
| 2007/0256700 A1* | 11/2007 | Bodelin | ............... | A45D 34/042 132/218 |
| 2008/0102047 A1* | 5/2008 | Appel | ................... | A61K 8/8176 424/63 |
| 2008/0124288 A1* | 5/2008 | Thevenet | ............... | A45D 33/00 424/63 |
| 2008/0241086 A1* | 10/2008 | Thevenet | ................. | A61K 8/19 424/63 |
| 2009/0081261 A1* | 3/2009 | Thevenet | ................. | A61K 8/19 424/401 |
| 2009/0116895 A1* | 5/2009 | Uehara | ................ | A45D 34/042 401/269 |
| 2009/0175813 A1 | 7/2009 | Morita et al. | | |
| 2009/0208443 A1 | 8/2009 | Polonka et al. | | |
| 2009/0317432 A1* | 12/2009 | Kergosien | ................ | A61K 8/02 424/401 |
| 2010/0031969 A1* | 2/2010 | Jager Lezer | ......... | A45D 40/262 132/200 |
| 2010/0089291 A1* | 4/2010 | Kang | ....................... | A61K 8/19 106/404 |
| 2010/0221204 A1* | 9/2010 | Morita | ..................... | A61K 8/19 424/63 |
| 2011/0070177 A1* | 3/2011 | Arnaud | ................ | A45D 34/041 424/63 |
| 2012/0251599 A1* | 10/2012 | Tranchant | ................ | A61Q 1/10 424/401 |
| 2013/0101538 A1* | 4/2013 | Nagasaka | ................ | A61K 8/19 424/63 |
| 2013/0330288 A1* | 12/2013 | Sato | ........................ | A61Q 1/10 424/63 |
| 2014/0020702 A1* | 1/2014 | Eguchi | ................... | A45D 40/00 132/200 |
| 2015/0007845 A1* | 1/2015 | Teboul | ............... | A45D 19/0008 132/200 |
| 2015/0016857 A1* | 1/2015 | Sato | ........................ | A61Q 1/10 401/16 |
| 2015/0117933 A1* | 4/2015 | Chen | .................... | A45D 34/042 401/283 |
| 2015/0216771 A1* | 8/2015 | Sakuma | ............... | A61K 8/0241 424/401 |

FOREIGN PATENT DOCUMENTS

| | | | |
|---|---|---|---|
| JP | 2010-132567 A | 6/2010 | |
| JP | 2010-260839 A | 11/2010 | |
| JP | 2011-512377 A | 4/2011 | |
| JP | 2011-140473 A | 7/2011 | |
| JP | WO 2012008009 A1 * | 1/2012 | .............. A61K 8/19 |
| WO | WO 2007/083753 A1 | 7/2007 | |
| WO | WO 2012/008009 A1 | 1/2012 | |

OTHER PUBLICATIONS

International Search Report (PCT/ISA/210) dated May 14, 2013, by the Japanese Patent Office as the International Searching Authority for International Application No. PCT/JP2013/054959.
"Personal Care Polymers—Product Catalog", Internet Citation. Jan. 1, 2000, pp. 1-16, XP002688408.
Extended European Search Report dated Nov. 2, 2015, by the European Patent Office in corresponding European Application No. 13754073.8 (6 pages).

* cited by examiner

LIQUID COSMETIC

TECHNICAL FIELD

The present invention relates to a liquid cosmetic, more specifically to a liquid cosmetic which is suited to a liquid cosmetic applicator using a brush or a pen feed as an applying means, which has a good water resistance and is excellent in a skin adhesive property and which is free of a lustrous feeling and has a mat tone.

BACKGROUND ART

Cosmetics prepared by dissolving dyes as a colorant in water, water-soluble organic solvents and the like and cosmetics prepared by dispersing pigments in water, water-soluble organic solvents and the like with surfactants and water-soluble resins have so far been known as liquid cosmetics of a type which is used by being stored in an applicator.

The above conventional liquid cosmetics are unsatisfactory in a water resistance when a dye is used. Also, when a pigment is used, a film-formable resin is added for fixing if a dispersant is a surfactant, and when a water-soluble resin is used for a dispersant, a water resistance is provided due to a fixing property of the dispersant.

However, cosmetics prepared by using pigments for conventional colorants and addition of film-formable resins for fixing and cosmetics prepared by using water-soluble resins for dispersants bring about the problems that they are still unsatisfactory in a water resistance and that the cosmetics are gradually lost when sweating, and the problem that a lustrous feeling is provided by addition of the film-formable resin is involved therein.

Then, the present applicants present a liquid cosmetic, more specifically to a liquid cosmetic which is suited to a liquid cosmetic applicator using a brush or a pen feed as an applying means and which has a good water resistance and is excellent in a skin adhesive property (refer to, for example, patent documents 1 and 2).

However, in the above liquid cosmetics, nothing has been referred to regarding a mat tone, and the cosmetics are different in compositions from the present invention.

Also, cosmetics characterized by comprising a polymer prepared by addition of a copolymer of acrylate and acryloyldimethyltaurinate salt to spherical polymethyl methacrylate are known as cosmetics (refer to, for example, patent document 3) which are excellent in an effect of providing a mat feeling and emulsion stabilization and which can be dispersed into a water phase and is improved in use feeling.

However, it is different from the present invention in the points that spherical polymethyl methacrylate is not required in the present invention and that the cosmetic of the present invention is not an emulsion type. Thus, the present invention is different from patent document 3 described above in a technical concept.

Further, known are cosmetics for a hairline between eyelashes which assists growth of eyelashes to obtain the long and beautiful eyelashes and can be applied without being sticky and which is provided with makeup effects such as an effect of endowing eyelashes with gloss, an effect of making eyelashes look thick, and the like by blending a hair growing agent such as a rhubarb extract and a stevia extract, a thickener such as hydroxymethyl cellulose, hydroxypropyl cellulose, succinoglycan, xanthan gum and a hydroxyethyl acrylate/acryloyldimethyltaurinato Na copolymer, and a film forming agent having a refractive index of 1.41 or more (refer to, for example, patent document 4).

In the above cosmetic, however, a transparency of the film is claimed in order to exert an effect of making eyelashes look thick as well as an effect of growing hairs by a hair growing agent such as a rhubarb extract and a stevia extract, and a pigment such as carbon black is not blended therein. Further, nothing has been referred to regarding a mat tone, and the above cosmetic is different in a composition from the present invention.

CONVENTIONAL ART DOCUMENTS

Patent Documents

Patent document 1: JP-A 2010-260839 (claims, examples and others)
Patent document 2: WO 2007/083753 (claims, examples and others)
Patent document 3: JP-A 2010-132567 (claims, examples and others)
Patent document 4: JP-A 2006-306854 (claims, examples and others)

DISCLOSURE OF THE INVENTION

Problems to be Solved by the Invention

In light of the problems on the conventional art and the present situation each described above, the present invention intends to solve problems, and an object thereof is to provide a liquid cosmetic which can be used for a liquid cosmetic applicator using a brush or a pen feed as an applying means, which is excellent in a water resistance and a skin adhesive property when applied and which is free of a lustrous feeling and has a mat tone.

Means to Solve the Problem

In light of the conventional problems described above and the like, intense researches repeated by the present inventors have resulted in finding that the object described above is achieved by a liquid cosmetic stored in a liquid cosmetic applicator using a brush or a pen feed as an applying means, wherein the above liquid cosmetic comprises at least a dispersant comprising a film-formable resin of an amount falling in a specific range, a film-forming agent and a surfactant in addition to carbon black and water; a specific component is added as a material for exerting an effect of a mat tone; and a glossiness and a viscosity of the liquid cosmetic are controlled to specific ranges. Thus, the present invention has been come to complete.

That is, the present invention resides in the following items (1) to (4).
(1) A liquid cosmetic stored in a liquid cosmetic applicator using a brush or a pen feed as an applying means, wherein the above liquid cosmetic comprises at least carbon black, water, 0.5 to 5% by mass of a dispersant comprising a film-formable resin, 2 to 15% by mass (in terms of a solid content) of a film-forming agent, 0.5% by mass or less of a surfactant, and xanthan gum or a hydroxyethyl acrylate/acryloyldimethyltaurinato Na copolymer as a material for exerting an effect of a mat tone; a glossiness of the liquid cosmetic is 6.5 or less; and a viscosity thereof measured at a temperature of 25° C. and a shear rate of 76.8 $s^{-1}$ by means of an EMD type viscometer falls in a range of 10 to 270 mPa·s.

(2) The liquid cosmetic as described in the above item (1), wherein the dispersant comprising the film-formable resin is a copolymer comprising monomers selected from one kind or two or more kinds of acrylic acid, methacrylic acid or alkyl esters or derivatives thereof, vinyl acetate and vinylpyrrolidone.

(3) The liquid cosmetic as described in the above item (2), wherein the dispersant comprising the film-formable resin is a copolymer of at least one of acrylic acid, methacrylic acid or alkyl esters or derivatives thereof with vinyl acetate, a copolymer of vinylpyrrolidone with vinyl acetate or a copolymer of at least one of acrylic acid, methacrylic acid or alkyl esters thereof with octylacrylamide.

(4) The liquid cosmetic as described in any one of the above items (1) to (3), wherein the liquid cosmetic is used for an eyeliner or an eyebrow.

Effect of the Invention

According to the present invention, provided is the specific effect that obtained is a liquid cosmetic of a black type color using carbon black as a colorant, which can be used for a liquid cosmetic applicator using a brush or a pen feed as an applying means, which is very excellent in a water resistant fixing property when applied and which provides a applied color of a mat tone without luster and is liable to draw fine lines.

DESCRIPTION OF THE PREFERRED EMBODIMENTS

Figure 1:
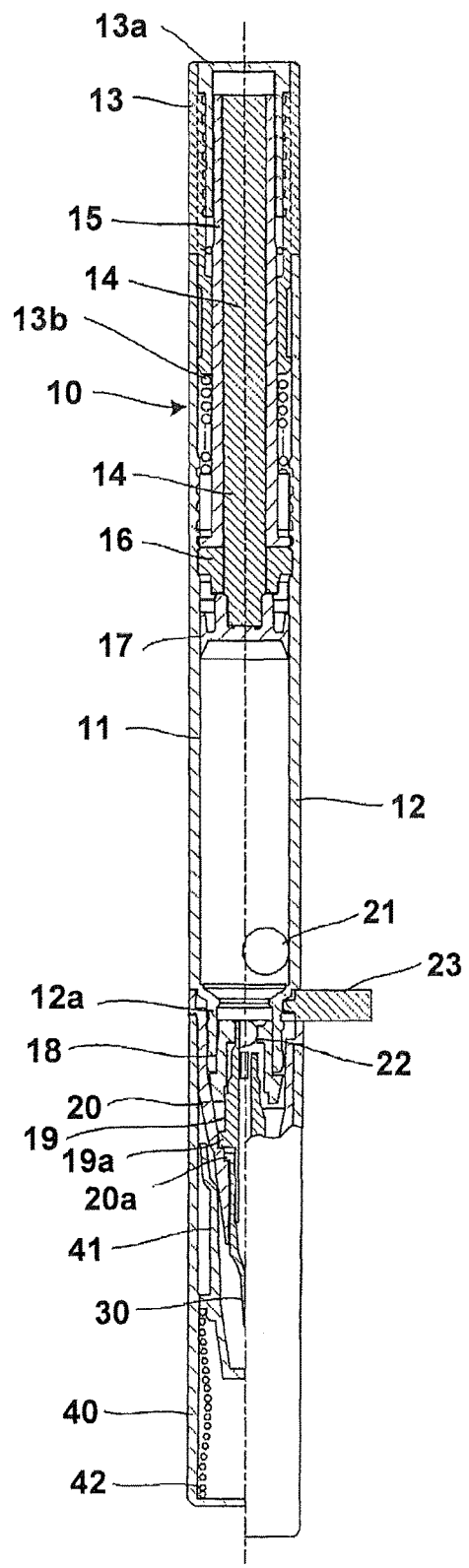
FIG. 1 is a partial cross section showing one example of the embodiment of the liquid cosmetic applicator used for the liquid cosmetic of the present invention.

The embodiments of the present invention shall be explained below in detail.

The liquid cosmetic of the present invention is characterized by that the invention is a liquid cosmetic stored in a liquid cosmetic applicator using a brush or a pen feed as an applying means, wherein the above liquid cosmetic comprises at least carbon black, water, 0.5 to 5% by mass of a dispersant comprising a film-formable resin, 2 to 15% by mass (in terms of a solid content) of a film-forming agent, 0.5% by mass or less of a surfactant and xanthan gum or a hydroxyethyl acrylate/acryloyldimethyltaurinato Na copolymer as a material for exerting an effect of a mat tone; a glossiness of the liquid cosmetic is 6.5 or less; and a viscosity thereof measured at a temperature of 25° C. and a shear rate of 76.8 $s^{-1}$ by means of an EMD type viscometer falls in a range of 10 to 270 mPa·s.

The carbon black used in the present invention is used as a colorant and shall not specifically be restricted as long as it is carbon black used usually as a colorant for black liquid cosmetics, and various carbon blacks can be used.

A content of the above carbon black is preferably 1 to 20% by mass, more preferably 5 to 15% by mass based on a total amount of the liquid cosmetic.

If a content of the above carbon black is less than 1% by mass, the color is palely developed and unsatisfactory for the cosmetic. On the other hand, if a content exceeds 20% by mass, the viscosity is increased too much, and the liquid is not smoothly discharged by the liquid cosmetic applicator of the present invention, so that it is not preferred.

The dispersant used in the present invention comprises a film-formable resin, and the dispersant enhances a dispersibility of the carbon black as a colorant and functions as a resin for forming a film.

The dispersant which can be used shall not specifically be restricted as long as the dispersant has the function described above, and the dispersant includes, for example, copolymers comprising monomers selected from one kind or two or more kinds of acrylic acid, methacrylic acid or alkyl esters or derivatives thereof, vinyl acetate and vinylpyrrolidone, and betaine type acrylic acid based amphoteric resins. The resin is preferably a copolymer of one kind selected from acrylic acid, methacrylic acid or alkyl esters or derivatives thereof with vinyl acetate, a copolymer of vinylpyrrolidone with vinyl acetate, and a copolymer of at least one of acrylic acid, methacrylic acid or alkyl esters thereof with octylacrylamide in terms of further enhancing a dispersing performance of the carbon black. The resin is particularly preferably a copolymer of at least one of acrylic acid, methacrylic acid or alkyl esters thereof with octylacrylamide in terms of further enhancing a dispersing performance and a film-forming ability thereof.

A content of the above dispersant is preferably 0.5 to 5% by mass, more preferably 2 to 4% by mass based on a total amount of the liquid cosmetic.

If a content of the above dispersant is less than 0.5% by mass, a dispersion stability of the carbon black as a colorant is unsatisfactory. On the other hand, if the dispersant is contained in an amount exceeding 5% by mass, the viscosity is increased too much, and the dispersion stability is not enhanced, so that it is not economical.

The film-forming agent used in the present invention includes, for example, emulsion resins of copolymers comprising monomers selected from one kind or two or more kinds of acrylic acid, methacrylic acid or alkyl esters or derivatives thereof, styrene and vinyl acetate.

In the present invention, the dispersant described above comprises as well a film-formable resin. The film-forming agent is different from the dispersant described above in terms of a soluble resin or an emulsion resin. The emulsion resin is an aqueous suspension obtained by subjecting a monomer to emulsion polymerization in water as a polymerization solvent. In dispersion of the carbon black in the present invention, a more stable emulsion of the carbon black is obtained in the soluble resin rather than in the emulsion resin. Thus, the resins are used in distinction from others by taking the above point into consideration.

A content of the film-forming agent (emulsion resin) is preferably 2 to 15% by mass, more preferably 2 to 10% by mass in terms of a solid content (resin content) based on a total amount of the liquid cosmetic.

If a content of the above film-forming agent (emulsion resin) is less than 2% by mass in terms of a solid content (resin content), the water resistant performance is deteriorated. On the other hand, if the film-forming agent is contained in an amount exceeding 15% by mass in terms of a solid content (resin content), an applying part (a brush, a pen feed and the like) of the liquid cosmetic applicator is dried to bring about the defect of being impossible to be applied in a certain case, and therefore it is not preferred.

A surfactant is used in a certain case for stabilizing the above film-forming agent (emulsion resin), but the surfactant blended with the above components exerts less influence on the fixing property in the present invention, so that it shall not be taken into consideration in terms of a content.

The surfactant used in the present invention is allowed to function as a dispersion auxiliary agent for dispersing the carbon black and includes, for example, nonionic surfactants, anionic surfactants and cationic surfactants, and the surfactant includes lecithin, propylene glycol fatty acid esters, glycerin fatty acid esters, polyglycerin fatty acid esters and in addition thereto, one kind or mixtures of two or more kinds of polyoxyethylene alkyl ethers, polyoxyethylene polyoxypropylene alkyl ethers, polyoxyethylene alkyl ether phosphoric acid.phosphate salt, polyethylene glycol fatty acid esters, alkylsulfate salt, sulfonate salt, polyoxyethylene alkyl ether sulfate salt and the like.

A content of the above surfactants is preferably 0.5% by mass or less, more preferably 0 to 0.3% by mass based on a total amount of the liquid cosmetic.

If the above surfactant is contained in an amount exceeding 0.5% by mass, the liquid cosmetic is inferior in a water resistance and cannot provide a sufficiently high adhesive property, and therefore it is not preferred.

The material for exerting an effect of a mat tone used in the present invention includes xanthan gum or a hydroxyethyl acrylate/acryloyldimethyltaurinato Na copolymer. The above material can provide the purposed applied color of a mat tone without luster at a low content, and the other materials, for example, silicic anhydride (silica), titanium dioxide and silicone particles exert less effect or cannot exert the effect.

The xanthan gum and the hydroxyethyl acrylate/acryloyldimethyltaurinato Na copolymer are used as thickeners for cosmetics in certain cases, and in the present invention, the xanthan gum and the hydroxyethyl acrylate/acryloyldimethyltaurinato Na copolymer are added in order to exert an effect of a mat-tone without luster.

The preferred ranges of the respective contents of the xanthan gum and the hydroxyethyl acrylate/acryloyldimethyltaurinato Na copolymer used are described below.

A content of the xanthan gum is preferably 0.05 to 0.7% by mass, more preferably 0.1 to 0.5% by mass and particularly preferably 0.2 to 0.4% by mass based on a total amount of the liquid cosmetic.

If a content of the xanthan gum is less than 0.05% by mass, the mat tone is deteriorated, and the lustrous feeling is exerted. On the other hand, if the xanthan gum is added in an excess of 0.7% by mass, the mat effect is not enhanced furthermore, and the viscosity is raised. Accordingly, both are not preferred.

Also, a content of the hydroxyethyl acrylate/acryloyldimethyltaurinato Na copolymer is preferably 0.05 to 1.1% by mass, more preferably 0.1 to 1.0% by mass and particularly preferably 0.3 to 0.7% by mass based on a whole amount of the liquid cosmetic.

If a content of the copolymer is less than 0.05% by mass, the mat tone is deteriorated, and the lustrous feeling is exerted. On the other hand, if the copolymer is added in an excess of 1.1% by mass, the mat effect is not enhanced furthermore, and it is not economical.

In the liquid cosmetic of the present invention, a viscosity thereof falls in a range of 10 to 270 mPa·s, and the range is preferably 20 to 250 mPa·s, more preferably 20 to 110 mPa·s.

If the above viscosity is less than 10 mPa·s, the liquid leaks in a certain case due to a low viscosity when impact such as falling is applied thereon. On the other hand, if the viscosity exceeds 270 mPa·s, the applying performance is deteriorated. Accordingly, both are not preferred.

The viscosity ranges described above can be controlled by a suitable combination of the carbon black, the kind of the dispersant comprising the film-formable resin, the kind of the film-forming agent, the kind of the surfactant, and the material for exerting an effect of a mat tone and combination of the respective contents in suitable ranges.

In the present invention, in respect to viscosity measuring conditions (including examples and others described later), to be specific, the viscosity was determined by measuring the obtained liquid cosmetic at a temperature of 25° C. by means of an EMD type viscometer manufactured by Toki Sangyo Co., Ltd. with a standard rotor: 20 rpm (shear rate: 76.8 [s$^{-1}$]).

A glossiness of the liquid cosmetic of the present invention falls in a range of 6.5 or less, preferably 5 or less and more preferably 4 or less. If the glossiness exceeds 6.5, a lustrous feeling is exerted on the applied color, and therefore it is not preferred. In respect to glossiness measuring conditions (including examples and others described later), to be specific, the glossiness was determined by measuring a coating film applied on a white part of a masking chart with a 80 μm applicator at a beam angle of 60° by means of a digital variable angle gloss meter UGV-5 manufacture by Suga Test Instruments Co., Ltd.

In the liquid cosmetic of the present invention, water (including refined water, distilled water, ion-exchanged water, purified water, ultra pure water and the like) is used as a solvent. A content of water is a balance obtained by deducting the amounts of the respective components described above and optional components described later from a total amount of the liquid cosmetic.

Further, optional components used for conventional liquid cosmetics in addition to the essential components described above can be contained in the liquid cosmetic of the present invention. To be specific, a preservative, an antioxidant, a neutralizer, a UV absorber, a chelating agent, a moisturizer, a beauty ingredient, a fragrance, a viscosity modifier and the like can be contained in suitable amounts as long as the effects of the present invention are not deteriorated.

The liquid cosmetic of the present invention can be produced by a conventional process, and the cosmetic can be used by filling in a liquid cosmetic applicator using a brush or a pen feed as an applying means.

The liquid cosmetic applicator which can be used shall not specifically be restricted as long as the applicator is a liquid cosmetic applicator equipped with a brush or a pen feed, for example, which is used for an eyeliner or an eyebrow.

The applicator includes preferably an applicator which is equipped with an applying body such as a brush (brush pencil) and a pen feed for an eyeliner or an eyebrow, and an applying means constituted from a rubber, an elastomer or a closed cell foam having a resilient property and which is provided with a container filled with a liquid cosmetic.

To be specific, preferably used is the liquid cosmetic applicator shown in FIG. 1 which is excellent in usability, a convenience and an applying property, wherein the applicator is provided with a liquid pressing mechanism of a rotary feeding type.

The liquid cosmetic applicator of the above type is provided, as shown in FIG. 1, with an applying part 30 formed by a brush (brush pencil) mounted in front of a liquid storing container 11 which is a storing part for the liquid cosmetic of the present invention (hereinafter referred to merely as the liquid cosmetic) stored in front of a liquid pressing mechanism 10, wherein the liquid cosmetic is discharged by the liquid pressing mechanism 10.

The liquid pressing mechanism 10 is constituted so that the liquid cosmetic in the container (storing part) 11 is fed by relatively rotating a feeding member 13 arranged in a rear end part of a holder main body 12 in a peripheral direction to the holder main body 12, whereby the liquid cosmetic is supplied to the applying part 30.

The liquid pressing mechanism 10 of the liquid cosmetic applicator is provided with the feeding member 13 rotatably interfitted with a rear end of the holder main body 12, a driving cylinder 15 conducting a rotating force of the feeding member 13 to a screw rod 14 by a user, a screw body 16 which is fixed to the holder main body 12 and with which the screw rod 14 is screwed, the screw rod 14 with which a piston body 17 is rotatably engaged at a tip, and the piston body 17 which slides in an inside of the storing part 11 of the holder main body 12. Assumed is the structure that the rotation of the feeding member 13 is conducted to the screw rod 14 via the driving cylinder 15. The rotation of the above screw rod 14 causes the screw rod 14 and the piston body 17 to move forward via a female screw of the nut-shaped screw body 16 to feed the liquid cosmetic from an inside of the storing part 11 to the applying part 30.

In the feeding member 13, a cylindrical operating part which is closed by inserting a crown 13a into a rear end is rotatably inserted, as shown in FIG. 1, into a rear end part of the holder main body 12, and is exposed. The driving cylinder 15 is inserted into the feeding member 13 and fixed in a rotational direction, and the screw body 16 is mounted with a fixed rotational direction and relatively rotatably to an axial direction in an inside of the driving cylinder 15. Symbol 13b is a spring member and pushes backward the feeding member 13 which is a rotating body.

In the above applicator, a sealing part 18, a joint member 19, a front holder 20 and the applying part 30 are mounted at a front end part 12a of the holder main body 12 by insertion. The liquid cosmetic is received in the storing part 11 of the holder main body 12, and the liquid cosmetic fed from the storing part 11 passes through a passage in the joint member 19 and is discharged into the applying part 30 to make it possible to apply. Also, a cap 40 is formed to be mounted (fit) on the front holder 20 covering the applying part 30 and the front holder 20 after use.

In FIG. 1, symbol 21 shows a stirring ball for stirring the liquid cosmetic in the storing part 11 by reciprocating-motion, and 22 shows a sealing ball. Also, 41 shows an inner cap in the cap 40, and 42 shows a spring for pushing backward the inner cap. The stirring ball 21 may be omitted.

Further, symbol 23 shows a stopper in which a ring-shaped part is mounted between a rear end of the front holder 20 and a front face of a step-wise site in the front end part 12a of the holder main body 12 in order to set the sealing part 18, the joint member 19, the front holder 20 and the applying part 30 in a position in which a passage of the liquid cosmetic flowing to the applying part 30 is closed when the applicator is unused. The ring-shaped part of the above stopper 23 is partially cut off, and a holding part is integrally formed at a side opposite to the cut-off part. The ring-shaped part is expanded in a diameter from the cut-off part by pulling the holding part and can be detached from a space between a rear end of the front holder 20 and the front end part 12a of the holder main body 12.

As shown in FIG. 1, when the applicator is unused, the sealing ball 22 is inserted into an inner diameter part of the sealing part 18 which is a receiving part for the ball to tightly seal so that the liquid cosmetic does not flow into an applying part 30 side. On the other hand, when the applicator is used, the stopper 23 is pulled out of the holder main body 12 and pushed into a rear end side of the front holder 20 by the user. Thus, a rear end narrow diameter part of the joint member 19 strikes against the sealing ball 22. Then, the sealing ball 22 is detached from the inner diameter part of the sealing part 18 and introduced into the storing part 11. The liquid cosmetic in the above storing part 11 flows into a liquid passage of the applying part 30 from an inner diameter part of the joint member 19. The liquid cosmetic is supplied from an inside thereof to the applying part 30 to make it possible to apply the liquid cosmetic on the object.

The liquid cosmetic applicator of the form described above has been explained with reference to the examples of the liquid cosmetic applicator for a liquid eyeliner and a liquid eyeshadow which are the liquid cosmetics of the present invention. However, the applicator shall not be restricted to examples. The cosmetic can be also applied as well to lines drawn on eyebrows by means of an eyebrow applicator and lines drawn on the skin.

The applicator of the rotary feeding type shown in FIG. 1 has been used as the liquid pressing mechanism in the liquid cosmetic applicator of the form described above. Also, an applicator of a knock feeding type shown, for example, in FIG. 2, which is excellent in usability, a convenience and an applying property may be used.

Figure 2:
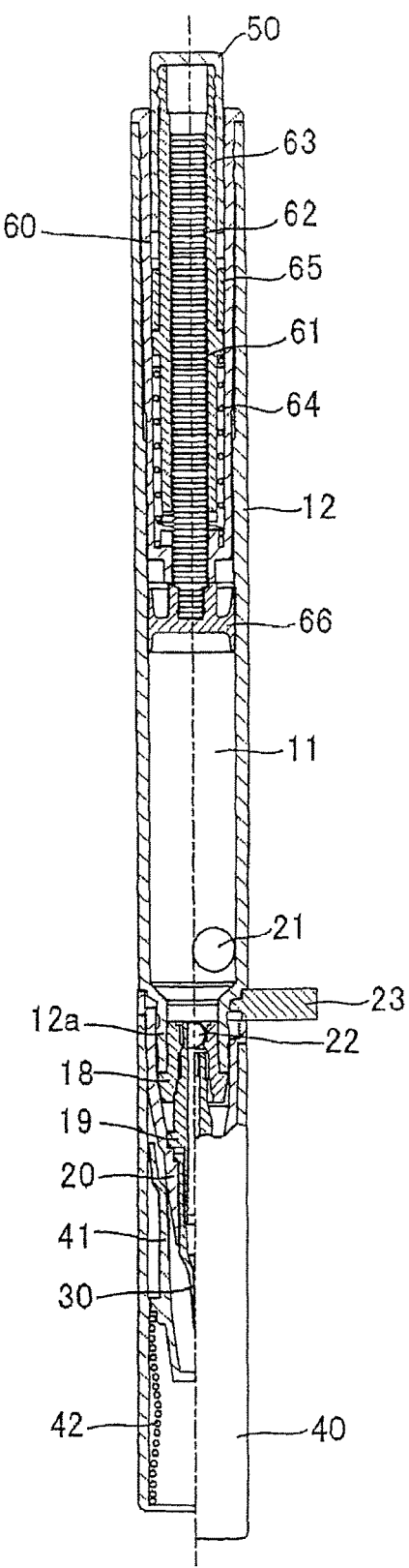
FIG. 2 is a partial cross section showing another example of the liquid cosmetic applicator used for the liquid cosmetic of the present invention.

FIG. 2 is an explanatory drawing of an applicator of a knock feeding type. In FIG. 2, same symbols are given to analogous parts as in the embodiment described above, and the explanations therefor are omitted.

In the applicator of a knock feeding type according to the above embodiment, a liquid cosmetic in a storing part 11 can be fed, as shown in FIG. 2, by pressing forward a knock member 50 mounted in a rear end part of a holder main body 12 in a holder direction. The applicator is provided with a knock mechanism part 60 for converting a pressing force of the knock member 50 exerted by knocking operation of the user to a rotational force by a cum mechanism, a screw body 61 fixed to the holder main body 12, and a screw rod 62 screwed with the screw body 61. The screw rod 62 is rotated by the pressing force converted by the knock mechanism part 60 to thereby cause the above screw rod 62 to move forward via the screw body 61, and the liquid cosmetic described above is fed. Also, the knock mechanism part 60 for converting a force exerted by pressing the knock member 50 to a rotational force comprises a rotational body 63 having first and second cum faces, the screw body 61 having a first fixed cum face, and a cum body 65 having a second fixed cum face as main constitutional factors.

In the above liquid cosmetic applicator of a knock feeding type, when the knock member 50 is pressed in a holder line direction to start knocking, the knock member 50 and the rotational body 63 start integrally moving forward while compressing a spring member 64. When knocking is further continued, the rotational body 63 moves forward while rotating in a prescribed direction. In the above case, the rotational body 63 is mounted rotatably in the knock member 50. Therefore, the knock member 50 itself does not rotate. The screw rod 62 which is regulated to a rotational direction of the rotational body 63 and which is provided movably in a holder line direction rotates integrally with the rotational body 63 as the rotational body 63 rotates in knocking. The screw rod 62 is screwed with the screw body 61, and therefore the screw rod 62 moves forward together with a piston body 66 to feed the liquid cosmetic in the storing part 11. Knocking is released from the above state. Knocking is released by causing the spring member 64 mounted in an inside of the screw body 61 to push up the rotational body 63. Meanwhile, the rotational body 63 starts rotating in a prescribed rotational direction and moving backward. Further, when releasing of knocking is continued, the rotational body 63 moves backward as well while rotating by a pushing-up force of the spring member 64. Also in the rotation, the screw rod 62 is rotated and moves forward, as described above, together with the piston body 66 to feed the liquid cosmetic. The knocking action and the releasing action in a holder line direction are converted into a rotational force by repeating the knocking action described above, and rotating the screw rod 62 to push out the piston body 66 makes it possible to feed constant amount of the liquid cosmetic to the applying part 30.

The liquid cosmetic of the present invention thus constituted is a liquid cosmetic stored in a liquid cosmetic applicator using a brush or a pen feed as an applying means, wherein the above liquid cosmetic comprises at least carbon black, water, 0.5 to 5% by mass of a dispersant comprising a film-formable resin, 2 to 15% by mass (in terms of a solid content) of a film-forming agent, 0.5% by mass or less of a surfactant, and xanthan gum or a hydroxyethyl acrylate/acryloyldimethyltaurinato Na copolymer as a material for exerting an effect of a mat tone; a glossiness of the liquid cosmetic is 6.5 or less; and a viscosity thereof measured at a temperature of 25° C. and a shear rate of 76.8 s$^{-1}$ by means of an EMD type viscometer falls in a range of 10 to 270 mPa·s. Accordingly, obtained is the liquid cosmetic which is very excellent in a water resistant fixing property when applied, which can draw lines of a mat tone without luster and is liable to draw fine lines and which is suitable for use in an eyeliner, an eyebrow or the like of a black type color using carbon black as a colorant.

EXAMPLES

Next, the present invention shall be explained in further details with reference to Examples and Comparative Examples, but the present invention shall not be restricted by the examples shown below.

Examples 1 to 9 and Comparative Examples 1 to 2

Liquid cosmetics (blend unit: % by mass, total amount: 100% by mass) having blend compositions shown in the following Table 1 were prepared to measure the viscosity values and the glossiness of the respective liquid cosmetics by the measuring method described above and evaluate a mat feeling, an applying performance, an aging stability of liquid contents and a water resistance thereof by the following respective evaluating methods.

The results thereof are shown in the following Table 1.

Evaluating Method of Mat Feeling:
The liquid cosmetic applicator of a brush pen type according to FIG. 1 was charged with the respective liquid cosmetics, and five lines having a width of 1 to 2 mm and a length of about 5 cm were drawn on a back of a hand to evaluate visually a mat feeling of the drawn lines by a sensory evaluation according to the following criteria.

Evaluation Criteria:
⊚: Lusterless mat lines are drawn
○: A little lustrous mat lines are drawn
Δ: Lustrous lines but are judged to fall in a scope of providing no unsatisfactory feeling are drawn
x: Lustrous lines providing an unsatisfactory feeling are drawn Evaluation Method of Applying Performance:
The liquid cosmetic applicator of a brush pen type according to FIG. 1 was charged with the respective liquid cosmetics, and five lines having a width of 1 to 2 mm and a length of about 5 cm were drawn on a back of a hand to evaluate applying performances (a drawn state and a drawn line intensity) according to the following evaluation criteria.

Evaluation Criteria:
⊚: drawn lines are intense and easy to draw
○: easy to draw and sufficiently intense
Δ: slight starving and blurring are observed, but judged to be within a practical scope
x: starving and blurring are observed, and felt unsatisfactory Evaluation Method of Aging Stability of Liquid Contents:
The respective liquid cosmetics which were liquid contents were stored in a thermostatic bath of 50° C. for 1 month, and then a viscosity thereof was measured. The above viscosity was compared with an initial viscosity value thereof to evaluate an aging stability of liquid contents thereof according to the following evaluation criteria.

Evaluation Criteria:
○: difference from the initial value is ±10% or less
Δ: difference from the initial value exceeds ±10% and is ±20% or less
x: difference from the initial value exceeds ±20%

Evaluating Method of Water Resistance:
The liquid cosmetic applicator of a brush pen type according to FIG. 1 was charged with the respective liquid cosmetics, and the liquid cosmetic was applied on a back of a hand. After the applied part was dried for 10 minutes, the applied part was exposed to flowing water to evaluate visually a peeling state of the applied part according to the following evaluation criteria.

Evaluation Criteria:
⊚: very good (the applied part was not peeled at all and very good)
○: good (the applied part was peeled a little and good)
Δ: average (the applied part was partially peeled)
x: inferior (the applied part was almost peeled)

TABLE 1

| Kind of composition | Specific compound name | Example | | | | | | | Comparative Example | | Example | |
|---|---|---|---|---|---|---|---|---|---|---|---|---|
| | | 1 | 2 | 3 | 4 | 5 | 6 | 7 | 1 | 2 | 8 | 9 |
| Pigment | Carbon black | 10 | 10 | 10 | 10 | 10 | 10 | 10 | 10 | 10 | 10 | 10 |
| Dispersant | Acrylic acid·octylacrylamide·acrylate ester copolymer | 3 | 3 | 3 | 3 | 3 | 3 | 3 | 3 | 3 | 3 | 3 |
| Surfactant | Polyoxyethylene behenyl ether | 0.3 | 0.3 | 0.3 | 0.3 | 0.3 | 0.3 | 0.3 | 0.3 | 0.3 | 0.3 | 0.3 |
| Film-forming agent emulsion | Alkyl acrylate copolymer emulsion*1 | 12 | 12 | 12 | 12 | 12 | 12 | 12 | 12 | 12 | 12 | 12 |
| | (resin content in emulsion) | 5 | 5 | 5 | 5 | 5 | 5 | 5 | 5 | 5 | 5 | 5 |
| Mat feeling provider | Xanthan gum | 0.3 | 0.2 | 0.1 | 0 | 0 | 0.05 | 0 | 0 | 0 | 0.7 | 0 |
| Mat feeling provider | Hydroxyethyl acrylate/acryloyldimethyltaurinato Na copolymer | 0 | 0 | 0 | 0.5 | 0.1 | 0 | 0.05 | 0 | 0 | 0 | 1.1 |

TABLE 1-continued

| Kind of composition | Specific compound name | Example 1 | 2 | 3 | 4 | 5 | 6 | 7 | Comparative Example 1 | 2 | Example 8 | 9 |
|---|---|---|---|---|---|---|---|---|---|---|---|---|
| Other mat feeling provider | Silica | 0 | 0 | 0 | 0 | 0 | 0 | 0 | 1 | 0 | 0 | 0 |
| Viscosity modifier | Smectite | 0 | 0 | 0 | 0 | 0 | 0 | 0 | 0 | 0.5 | 0 | 0 |
| Neutralizer | Aminomethylpropanol | 0.3 | 0.3 | 0.3 | 0.3 | 0.3 | 0.3 | 0.3 | 0.3 | 0.3 | 0.3 | 0.3 |
| Chelating agent | Disodium EDTA | 0.3 | 0.3 | 0.3 | 0.3 | 0.3 | 0.3 | 0.3 | 0.3 | 0.3 | 0.3 | 0.3 |
| Moisturizer | 1,3-butylene glycol | 8 | 8 | 8 | 8 | 8 | 8 | 8 | 8 | 8 | 8 | 8 |
| Preservative | Methylparaben | 0.4 | 0.4 | 0.4 | 0.4 | 0.4 | 0.4 | 0.4 | 0.4 | 0.4 | 0.4 | 0.4 |
| Preservative | Sodium dehydroacetate | 0.1 | 0.1 | 0.1 | 0.1 | 0.1 | 0.1 | 0.1 | 0.1 | 0.1 | 0.1 | 0.1 |
| Water | Refined water | Balance | | | | | | | Balance | | Balance | |
| Viscosity (mPa·s) | Shear rate: 76.8 ($s^{-1}$) | 108 | 47 | 28 | 25 | 22 | 17 | 14 | 6 | 118 | 261 | 31 |
| Glossiness | | 2.8 | 3.6 | 4.5 | 2.2 | 4.8 | 5.9 | 6.4 | 17.5 | 10.8 | 1.3 | 1.9 |
| Mat feeling | | ◎ | ◎ | ○ | ○ | ○ | △ | △ | X | X | ◎ | ◎ |
| Applying performance | | ◎ | ◎ | ○ | ◎ | ○ | △ | △ | X | ○ | △ | △ |
| Aging stability of liquid contents | | ○ | ○ | ○ | ○ | ○ | ○ | ○ | ○ | ○ | △ | ○ |
| Water resistance | | ◎ | ◎ | ◎ | ○ | ◎ | ◎ | ◎ | ◎ | ◎ | ○ | △ |

*1 copolymer emulsion comprising two or more components of acrylic acid, methacrylic acid or (C1 to C4 and C8) alkyl esters thereof.

As apparent from the results shown in Table 1 described above, it has become clear that the liquid cosmetics prepared in Examples 1 to 9 falling in the scope of the present invention cause a glossiness, an applying performance, an aging stability of liquid contents and a water resistance to be compatible to a high degree as compared with the liquid cosmetics prepared in Comparative Examples 1 to 2 out of the scope of the present invention and that in addition thereto, Examples are excellent in a mat feeling.

To observe individually the Comparative examples, in Comparative Example 1, the other material out of the scope of the present invention was blended as the mat feeling provider, and in Comparative Example 2, the viscosity range fell in the scope of the present invention, but the mat feeling provider was not added, and the targeted purposed mat feeling was not obtained. It has been found that the effects of the present invention cannot be exerted in the above cases

INDUSTRIAL APPLICABILITY

Obtained is a liquid cosmetic stored in a liquid cosmetic applicator suited for use in an eyeliner or an eyebrow applied by using a brush or a pen feed as an applying means.

LETTERS AND NUMERALS

10 Liquid pressing mechanism
12 Holder main body
13 Feeding member
17 Piston
18 Sealing part
10 Joint member
20 Front holder
30 Applying part (brush)

The invention claimed is:

1. A liquid eyeliner or eyebrow cosmetic stored in a liquid cosmetic applicator using a brush or a pen feed as an applying means,
    wherein the liquid cosmetic comprises at least:
    carbon black,
    water,
    0.5 to 5% by mass of a dispersant comprising a soluble film-formable resin selected from the following group A,
    2 to 15% by mass (in terms of a solid content) of a film-forming agent of an emulsion resin of a copolymer of one or more monomer selected from the following group B,
    0.5% by mass or less of a surfactant, and
    xanthan gum or a hydroxyethyl acrylate/acryloyldimethyltaurinato Na copolymer as a material for exerting an effect of a mat tone; and
    wherein
    a glossiness of the liquid cosmetic is 6.5 or less; and
    a viscosity of the liquid cosmetic thereof measured at a temperature of 25° C. and a shear rate of 76.8 $s^{-1}$ by means of an EMD type viscometer falls in a range of 10 to 270 mPa·s,
    group A: a copolymer of at least one of acrylic acid, methacrylic acid, alkyl ester of acrylic acid, alkyl ester of methacrylic acid, derivative of acrylic acid, or derivative of methacrylic acid with vinyl acetate, a copolymer of vinylpyrrolidone with vinyl acetate, or a copolymer of at least one of acrylic acid, methacrylic acid, alkyl ester of acrylic acid, or alkyl ester of methacrylic acid with octylacrylamide,
    group B: acrylic acid, methacrylic acid, alkyl ester of acrylic acid, alkyl ester of methacrylic acid, derivative of acrylic acid, derivative of methacrylic acid, styrene, and vinyl acetate.

2. The liquid cosmetic as described in claim 1, wherein the liquid cosmetic applicator is provided with a container for holding the liquid cosmetic.

3. The liquid cosmetic as described in claim 1, wherein the liquid cosmetic comprises 0.05 to 0.7% by mass of xanthan gum or 0.05 to 1.1% by mass of a hydroxyethyl acrylate/acryloyldimethyltaurinato Na copolymer.

4. The liquid cosmetic as described in claim 3, wherein the liquid cosmetic applicator is provided with a container for holding the liquid cosmetic.

5. The liquid eyeliner or eyebrow cosmetic as described in claim 1, which is a cosmetic to draw a line on a skin.

* * * * *